(12) United States Patent
Briggs et al.

(10) Patent No.: US 10,918,802 B2
(45) Date of Patent: Feb. 16, 2021

(54) NEEDLE EXCHANGE SYSTEM

(71) Applicant: A TO Z TECHNOLOGIES, LLC, Midland, SD (US)

(72) Inventors: Aaron Cole Briggs, Midland, SD (US); Zay Norman, Hayes, SD (US)

(73) Assignee: A to Z Technologies, LLC, Midland, SD (US)

( * ) Notice: Subject to any disclaimer, the term of this patent is extended or adjusted under 35 U.S.C. 154(b) by 0 days.

(21) Appl. No.: 16/506,005

(22) Filed: Jul. 9, 2019

(65) Prior Publication Data
US 2020/0188606 A1 Jun. 18, 2020

Related U.S. Application Data

(63) Continuation-in-part of application No. 16/221,096, filed on Dec. 14, 2018, now abandoned.

(51) Int. Cl.
*A61M 5/32* (2006.01)

(52) U.S. Cl.
CPC ........ *A61M 5/3202* (2013.01); *A61M 5/3213* (2013.01); *A61M 5/3269* (2013.01); *A61M 2005/3247* (2013.01)

(58) Field of Classification Search
CPC .............. A61M 5/3204; A61M 5/3213; A61M 2005/3215; A61M 2005/3247; A61M 5/3278; A61M 5/3202; A61M 5/3269
USPC .................. 604/110, 192; 206/210, 366, 364
See application file for complete search history.

(56) References Cited

U.S. PATENT DOCUMENTS

| | | | |
|---|---|---|---|
| 4,610,667 A | | 9/1986 | Pedicano |
| 4,623,336 A | | 11/1986 | Pedicano |
| 4,629,453 A | * | 12/1986 | Cooper ............... A61M 5/3213 604/192 |
| 4,911,694 A | | 3/1990 | Dolan |
| 4,973,315 A | | 11/1990 | Sincock |
| 5,002,536 A | | 3/1991 | Thompson |
| 5,037,400 A | | 8/1991 | Curry |
| 5,037,402 A | | 8/1991 | Bartman |
| 5,084,027 A | * | 1/1992 | Bernard ............. A61M 5/3213 206/365 |

(Continued)

FOREIGN PATENT DOCUMENTS

| | | |
|---|---|---|
| CA | 2087362 | 7/1994 |
| WO | 9740869 | 11/1997 |
| WO | 2018106686 | 6/2018 |

*Primary Examiner* — Chun Hoi Cheung
(74) *Attorney, Agent, or Firm* — Jeffrey A. Proehl; Woods, Fuller, Shultz & Smith PC

(57) ABSTRACT

A system for facilitating exchange of needles on syringes may include a needle exchange device forming a pair of needle sheaths with each needle sheath defining an insertion opening and a channel in communication with the insertion opening to receive at least a portion of a needle device. One of the needle sheaths may be a dispensing needle sheath for dispensing a needle device to be used for the syringe, another one of the needle sheaths being a disposal needle sheath for receiving a needle device to be disposed. The needle exchange device may be elongated along a longitudinal axis with opposite first and second ends. The system may also include a needle device removably positioned in the dispensing needle sheath. The disposal needle sheath and the dispensing needle sheath may be substantially oppositely oriented on the exchange device.

18 Claims, 5 Drawing Sheets

(56) References Cited

U.S. PATENT DOCUMENTS

| | | | |
|---|---|---|---|
| 5,099,992 A * | 3/1992 | Heimreid | A61J 1/2096 |
| | | | 206/366 |
| 5,163,915 A | 11/1992 | Holleron | |
| 5,190,532 A * | 3/1993 | Yu | A61M 5/3213 |
| | | | 604/192 |
| 5,343,875 A | 9/1994 | Chase | |
| 5,505,705 A * | 4/1996 | Galpin | A61M 5/3213 |
| | | | 604/192 |
| 5,554,129 A * | 9/1996 | Stevenson | A61M 5/3213 |
| | | | 604/110 |
| 5,558,649 A * | 9/1996 | Shields | A61M 5/3213 |
| | | | 604/192 |
| 5,562,625 A | 10/1996 | Stefancin, Jr. | |
| 6,036,675 A | 3/2000 | Thorne | |
| 6,279,743 B1 * | 8/2001 | Ballard | A61M 5/3213 |
| | | | 128/852 |
| 6,315,113 B1 * | 11/2001 | Britton | A61M 5/3202 |
| | | | 204/275.1 |
| 7,063,683 B2 * | 6/2006 | Teringo | A61M 5/3213 |
| | | | 604/110 |
| 7,665,605 B2 | 2/2010 | Erickson | |
| 9,492,622 B2 | 11/2016 | Brereton | |
| 9,656,026 B2 | 5/2017 | Bostrom | |
| 9,808,575 B2 | 11/2017 | McLoughlin | |
| 2010/0063457 A1 | 3/2010 | Crossman | |
| 2015/0119818 A1 | 4/2015 | Evans | |

\* cited by examiner

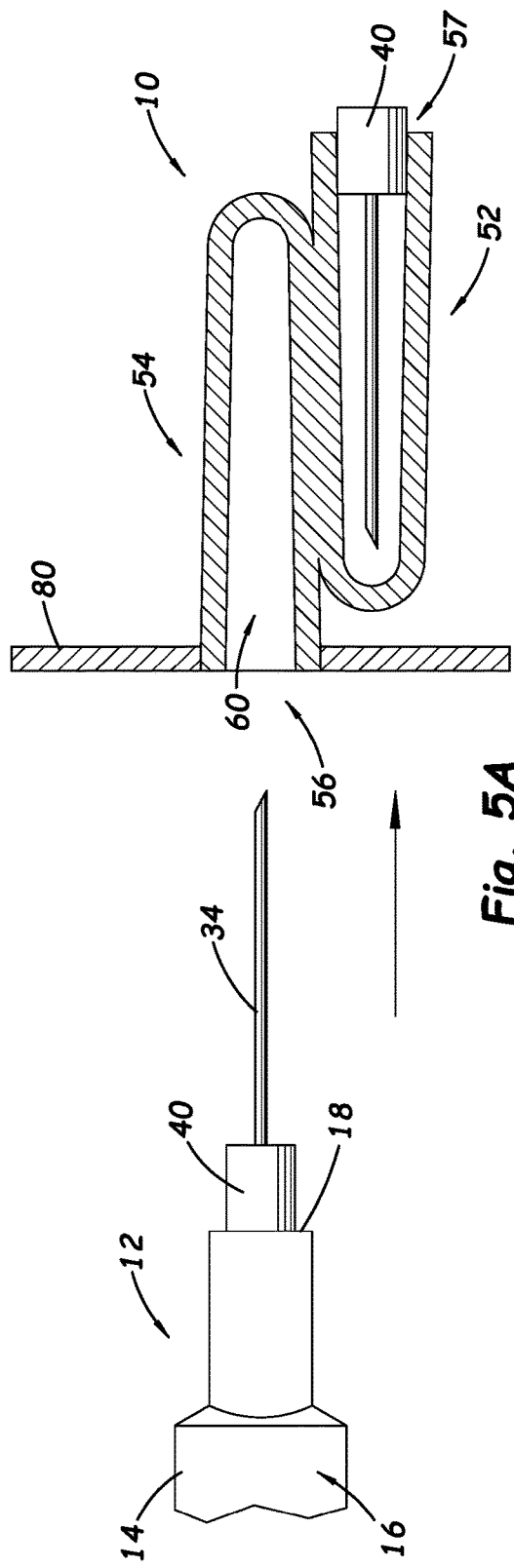
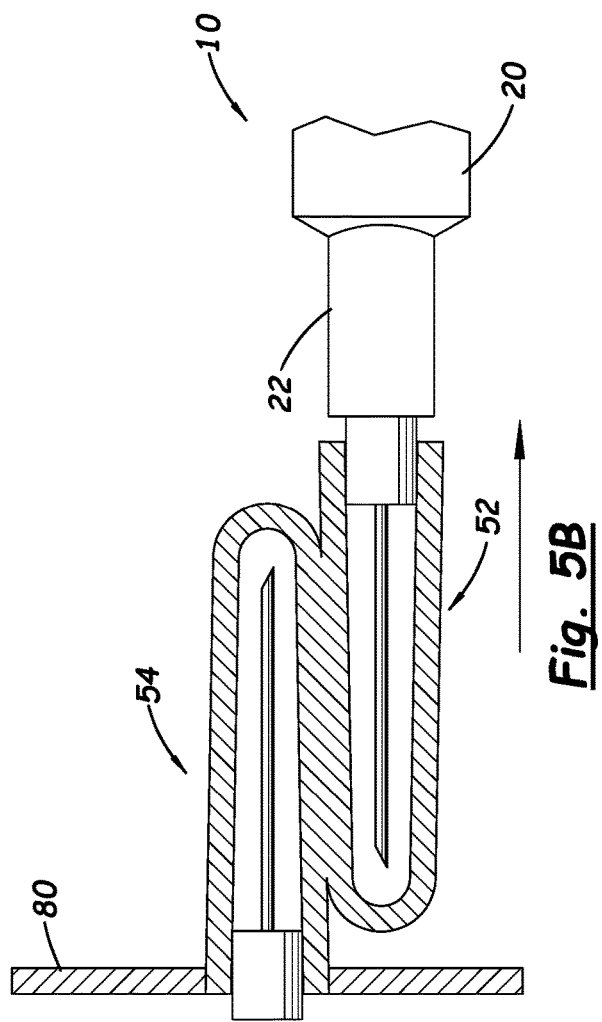

NEEDLE EXCHANGE SYSTEM

REFERENCE TO RELATED APPLICATIONS

This application is a continuation-in-part of U.S. patent application Ser. No. 16/221,096 filed Dec. 14, 2018, which is hereby incorporated by referenced in its entirety

BACKGROUND

Field

The present disclosure relates to syringe safety products and more particularly pertains to a new needle exchange system for facilitating easier and safer removal and exchange of needles, such as hypodermic needles, on syringes and other devices utilizing needles.

SUMMARY

In one aspect, the present disclosure relates to a system for facilitating exchange of needles on syringes. The system may comprise a needle exchange device forming a pair of needle sheaths, with each needle sheath defining an insertion opening and a channel in communication with the insertion opening to receive at least a portion of a needle device. One of the needle sheaths may be a dispensing needle sheath for dispensing a needle device to be used for the syringe and another one of the needle sheaths may be a disposal needle sheath for receiving a needle device to be disposed. The needle exchange device may be elongated along a longitudinal axis with opposite first and second ends. The system may also include a needle device removably positioned in the dispensing needle sheath. The disposal needle sheath and the dispensing needle sheath may be substantially oppositely oriented on the exchange device.

In another aspect, the present disclosure relates to a system for facilitating exchange of needles on syringes. The system my comprise a needle exchange device forming a pair of needle sheaths, with each needle sheath defining an insertion opening and a channel in communication with the insertion opening to receive at least a portion of a needle device. One of the needle sheaths may be a dispensing needle sheath for dispensing a needle device to be used for the syringe and another one of the needle sheaths may be a disposal needle sheath for receiving a needle device to be disposed. The needle exchange device may be elongated along a longitudinal axis with opposite first and second ends. The system may also include a needle device removably positioned in the dispensing needle sheath. The system may also include a needle device removably positioned in the dispensing needle sheath, and a finger shield positioned adjacent to the insertion opening of the disposal needle sheath to protect fingers of the user gripping the needle exchange device. The disposal needle sheath of the needle exchange device may be empty of any needle device. The disposal needle sheath and the dispensing needle sheath are substantially oppositely oriented on the exchange device such that the insertion openings of the disposal needle sheath and the dispensing needle sheath are located at longitudinally opposite locations on the exchange device.

In still another aspect, the disclosure relates to a system which may comprise a syringe including a plunger and a barrel with a main portion defining a major portion of an interior of the barrel and a transition portion, and the transition portion may have a first mounting structure. The system may further include a first needle device removably mounted on the syringe and comprising a needle and a mounting hub. The mounting hub may have a second mounting structure complementary to the first mounting structure and configured to removably mount on the transition portion of the barrel. The system may further include a needle exchange device forming a pair of needle sheaths with each needle sheath defining an insertion opening and a channel in communication with the insertion opening to receive at least a portion of a needle device. One of the needle sheaths may be a dispensing needle sheath for dispensing a needle device to be used for the syringe and another one of the needle sheaths may be a disposal needle sheath for receiving a needle device to be disposed. The needle exchange device may be elongated along a longitudinal axis with opposite first and second ends. The system may also include a second needle device removably positioned in the dispensing needle sheath, and the disposal needle sheath of the needle exchange device may be empty of any needle device. The disposal needle sheath and the dispensing needle sheath may be substantially oppositely oriented on the exchange device such that the insertion openings of the disposal needle sheath and the dispensing needle sheath are located at longitudinally opposite locations on the exchange device.

In yet another aspect, the disclosure relates to a system for facilitating exchange of needles on syringes which may comprise a needle exchange device elongated along a longitudinal axis with opposite first and second ends. The exchange device may form a needle sheath defining an insertion opening and an elongated channel in communication with the insertion opening to receive at least a portion of a needle device mounted on a syringe to be discarded. The needle exchange device may form a needle assembly pocket which defines an elongated dispensing cavity for removably receiving at least a portion of a needle assembly with a needle device to be mounted on a syringe, and the dispensing cavity may have a cavity opening. An axis along which the channel of the needle sheath is elongated and an axis along which the cavity of the needle assembly pocket is elongated may be oriented substantially parallel to the longitudinal axis of the needle exchange device. The needle sheath and the needle assembly pocket may be substantially oppositely oriented on the exchange device such that the insertion opening of the needle sheath is located at the first end of the needle exchange device and the cavity opening of the needle assembly pocket is located at the second and of the needle exchange device.

In still yet another aspect, the disclosure relates to a system which may comprise a syringe including a plunger and a barrel with a main portion defining a major portion of an interior of the barrel and a transition portion, and the transition portion may have a first mounting structure. The system may also include a first needle device removably mounted on the syringe, and the first needle device may comprise a needle and a mounting hub which may have a second mounting structure complementary to the first mounting structure and configured to removably mount on the transition portion of the barrel. The system may also include a needle exchange device elongated along a longitudinal axis with opposite first and second ends, and the exchange device may form a needle sheath defining an insertion opening and an elongated channel in communication with the insertion opening to receive at least a portion of a needle device mounted on a syringe to be discarded. The needle exchange device may form a needle assembly pocket defining an elongated dispensing cavity for removably receiving at least a portion of a needle assembly with a needle device to be mounted on a syringe. The dispensing cavity may have a cavity opening. An axis along which the channel of the needle sheath is elongated and an axis along which the cavity of the needle assembly pocket is elongated may be oriented substantially parallel to the longitudinal axis of the needle exchange device. The needle sheath and the needle assembly pocket may be substantially oppositely oriented on the exchange device such that the insertion opening of the needle sheath is located at the first end of the needle exchange device and the cavity opening of the needle assembly pocket is located at the second and of the needle exchange device. The system may also include a needle assembly including a needle device with a needle and a protective sleeve positioned over at least the needle of the needle device, and the protective sleeve may be at least partially inserted into the dispensing cavity of the needle assembly pocket.

There has thus been outlined, rather broadly, some of the more important elements of the disclosure in order that the detailed description thereof that follows may be better understood, and in order that the present contribution to the art may be better appreciated. There are additional elements of the disclosure that will be described hereinafter and which will form the subject matter of the claims appended hereto.

In this respect, before explaining at least one embodiment or implementation in greater detail, it is to be understood that the scope of the disclosure is not limited in its application to the details of construction and to the arrangements of the components, and the particulars of the steps, set forth in the following description or illustrated in the drawings. The disclosure is capable of other embodiments and implementations and is thus capable of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

The advantages of the various embodiments of the present disclosure, along with the various features of novelty that characterize the disclosure, are disclosed in the following descriptive matter and accompanying drawings.

BRIEF DESCRIPTION OF THE DRAWINGS

The disclosure will be better understood and when consideration is given to the drawings and the detailed description which follows. Such description makes reference to the annexed drawings wherein:

FIG. 5A is a schematic side sectional view of the exchange system with the syringe shown entering the disposal sheath of the exchange device, according to an illustrative embodiment.

FIG. 5B is a schematic side sectional view of the exchange system with the syringe shown engaging a needle device positioned in the dispensing sheath of the exchange device, according to an illustrative embodiment.

DETAILED DESCRIPTION

Figure 1:
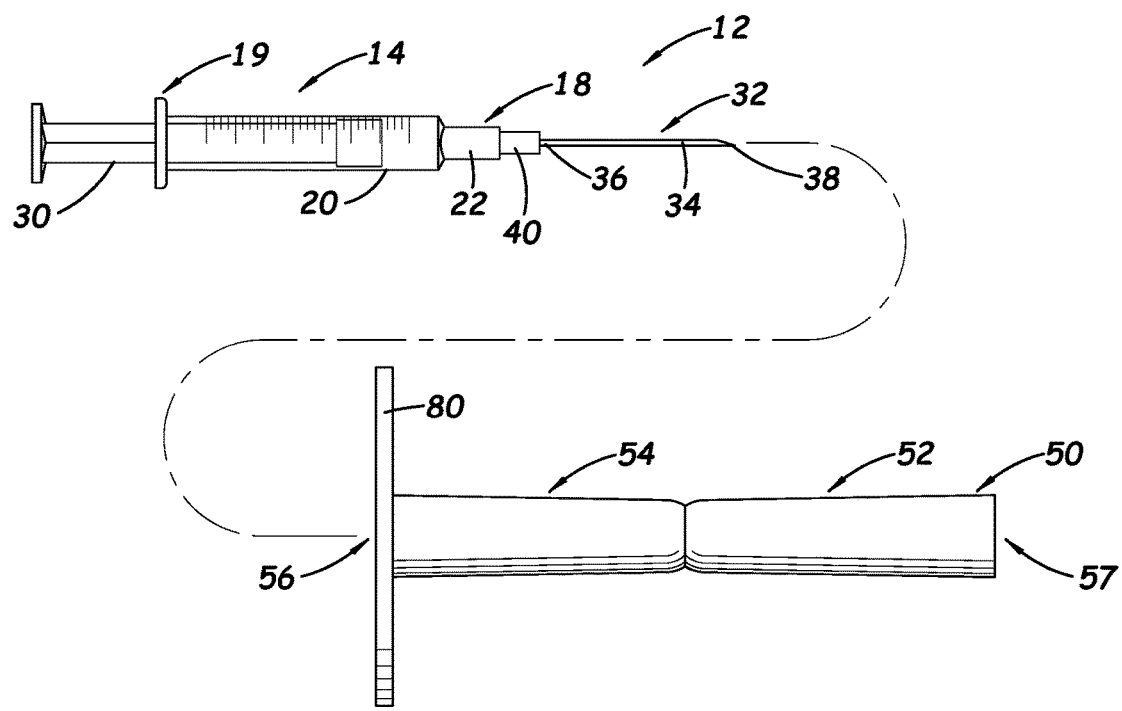
FIG. 1 is a schematic side view of a new needle exchange system according to the present disclosure.
Figure 2:
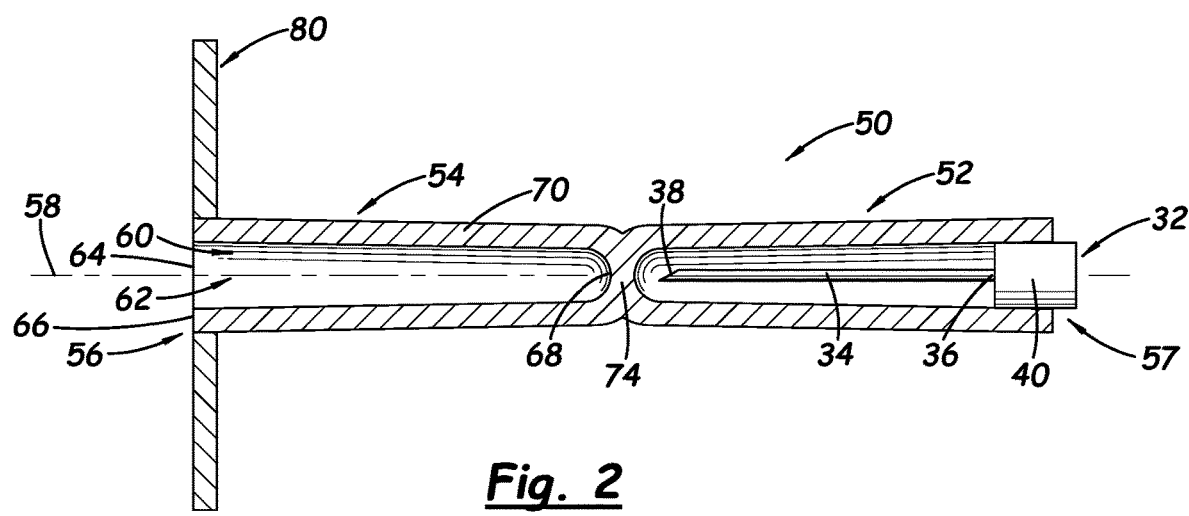
FIG. 2 is a schematic side sectional view of the needle exchange device, according to an illustrative embodiment.
Figure 3:
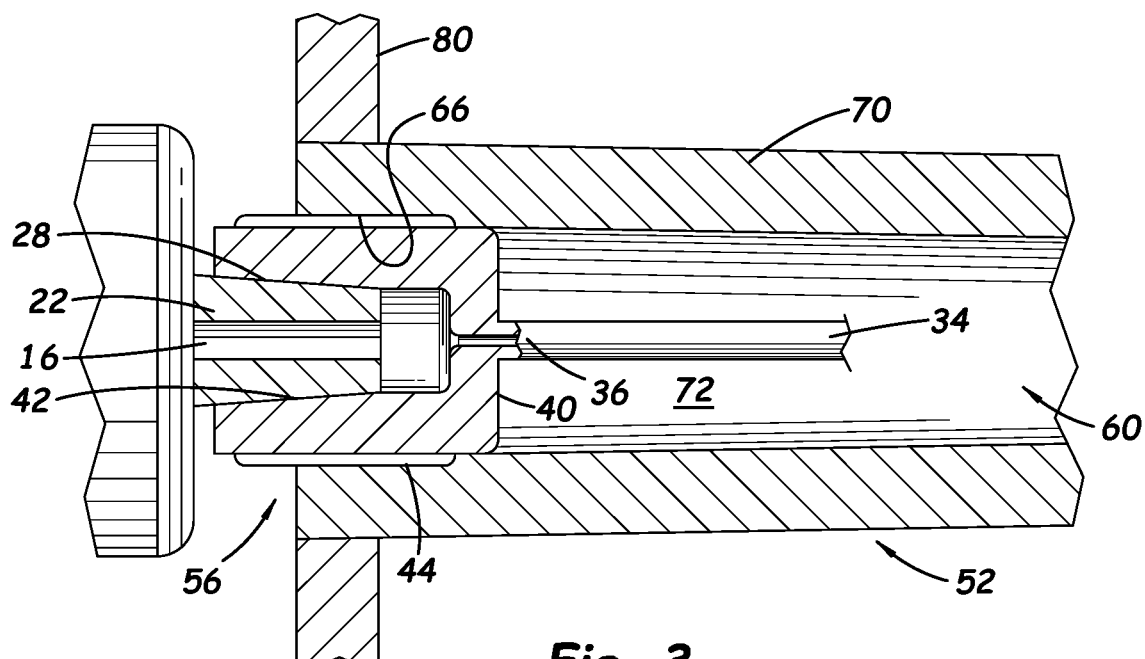
FIG. 3 is a schematic side sectional view of a portion of the system, according to an illustrative embodiment.
Figure 4:
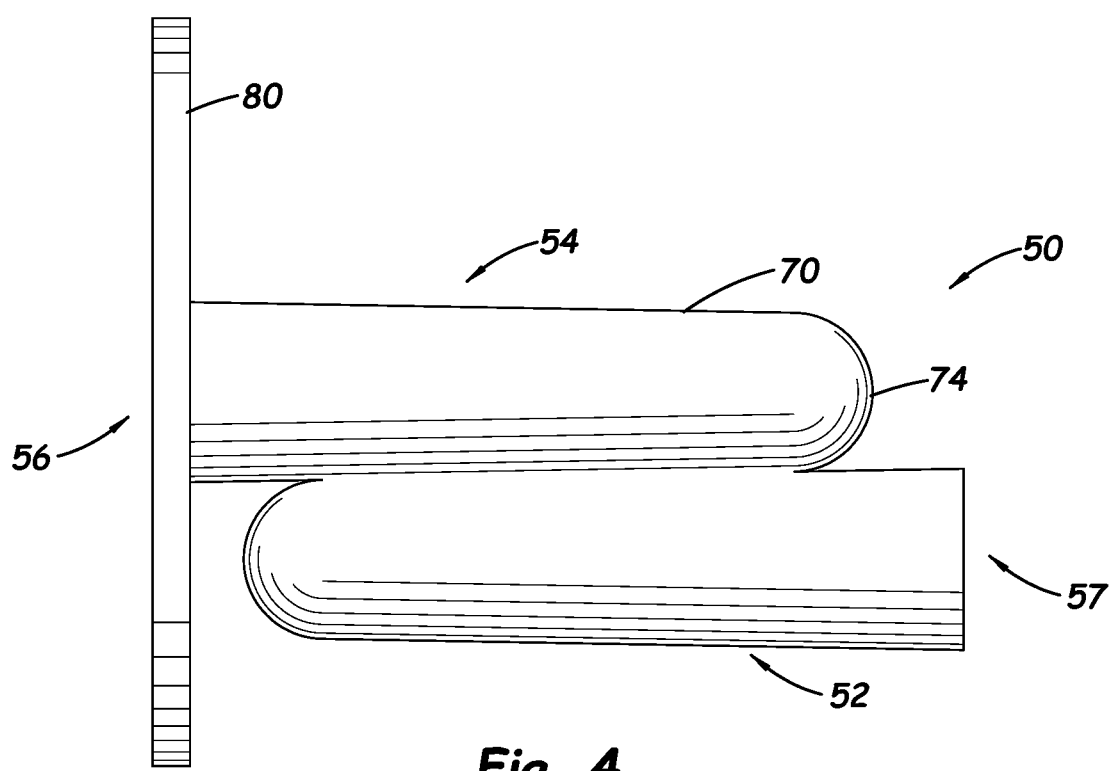
FIG. 4 is a schematic side view of the needle exchange device, according to an illustrative embodiment.
Figure 6:
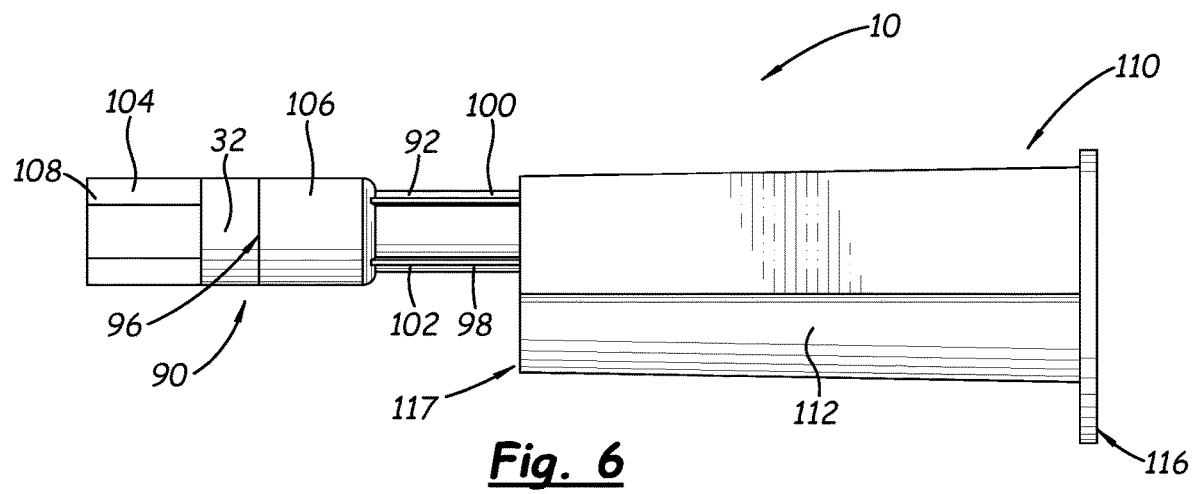
FIG. 6 is a schematic side view of another illustrative embodiment of the exchange system with a needle assembly and a needle device.
Figure 7:
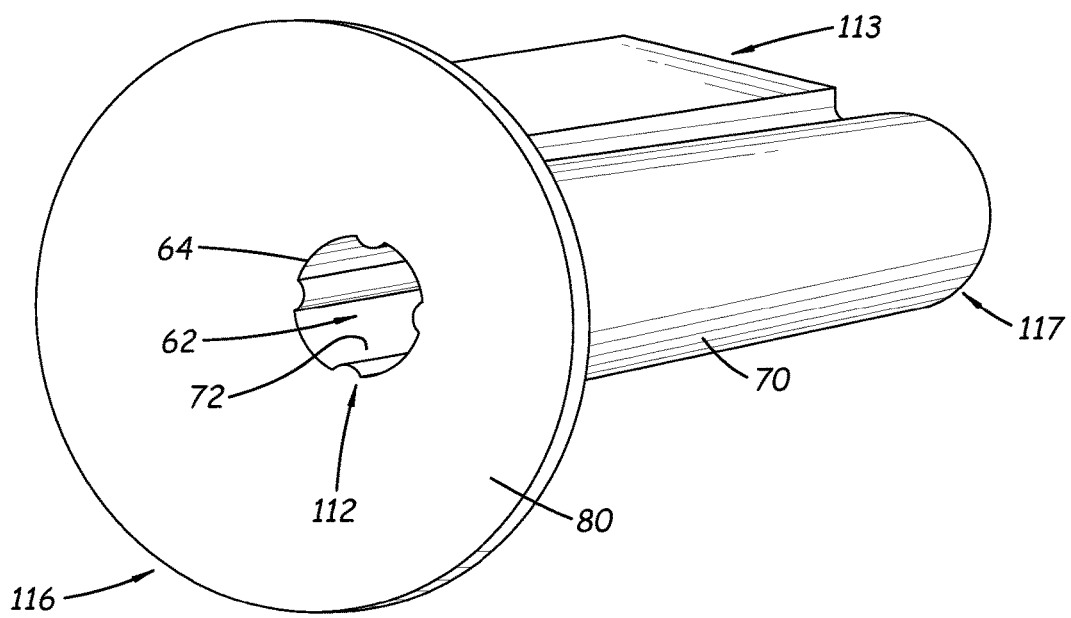
FIG. 7 is a schematic perspective view of the needle exchange device from a first end viewpoint, according to an illustrative embodiment.
Figure 8:
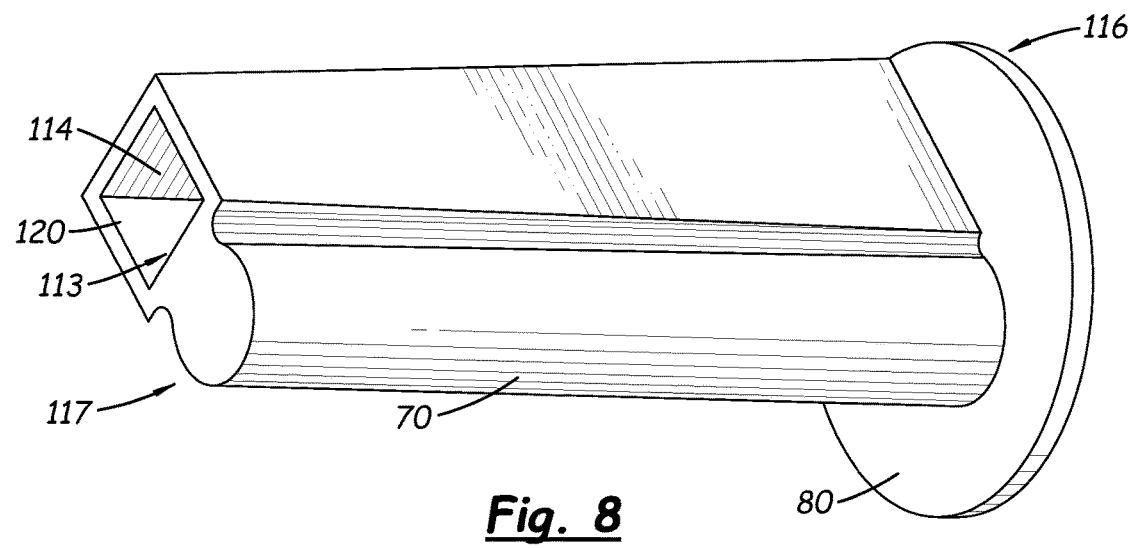
FIG. 8 is schematic perspective view of the needle exchange device from a second end viewpoint, according to an illustrative embodiment.
Figure 9:
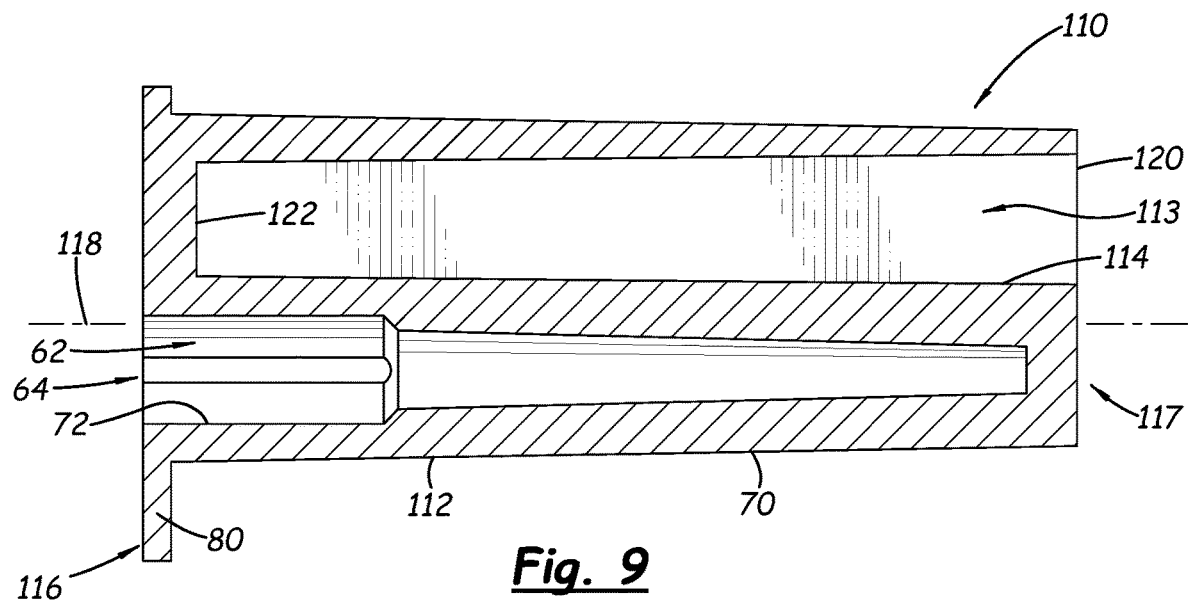
FIG. 9 is a schematic side sectional view of the needle exchange device, according to an illustrative embodiment.

With reference now to the drawings, and in particular to FIGS. 1 through 9 thereof, a new needle exchange system embodying the principles and concepts of the disclosed subject matter will be described.

The applicants have recognized that inoculating livestock can potentially be hazardous not only from the risk inherent in handling a sharpened needle, but also from the jostling movement of the livestock which generally does not exist when injecting a human. The inoculation or vaccination task becomes especially dangerous when exchanging an older used needle for a new unused needle on a syringe in the midst of inoculating large numbers of livestock.

The applicants have thus devised a needle exchange system 10 utilizing a unique needle exchange device 50 which facilitates the ease with which a needle already mounted on a syringe may be exchanged for another needle, and also greatly enhances the safety with which such a test can be performed.

In one aspect, the system 10 includes a syringe 12 of conventional design utilizing a barrel 14 which defines an interior 16 for receiving a fluid to be injected into the flesh of a being, and may have a proximal end 18 and a distal end 19. Typically, the barrel will include a main portion 20 defining a major portion of the interior 16 and having an opening into the interior which may be located at the proximal end of the barrel. The barrel 14 may also include a transition portion 22 which is configured for mounting a needle thereon and may be mounted on the barrel at a location opposite of the opening at the proximal end. The transition portion may also have a passage in fluid communication with the main portion of the interior 16 and which may terminate at an aperture at the distal end 18 of the transition portion of the barrel.

A first mounting structure 28 may be located on the transition portion to permit mounting of a needle on the syringe, and the structure 28 may be located on the exterior of a section of the transition portion. In some embodiments, the first mounting structure 28 may comprise a friction connection, and may be characterized by a slight taper in the width of the outer surface of the transition portion toward the distal end 18. In other embodiments, threads may be formed on the exterior the transition portion for interacting with threads on the needle.

The syringe 12 may further include a plunger 30 which is movably mounted on the barrel to move the contents of the interior 16 of the barrel through the passage and aperture of the transition portion. The plunger 30 may pass through the opening of the barrel and have a portion located in the interior 16 of the barrel.

A needle device 32 may be mounted on the syringe 12 and may include a needle 34 which has a base end 36 and an injection tip 38 located opposite of the base end, and a mounting hub 40 located at the base end of the needle which is configured to removably mount on the barrel, and particularly the transition portion of the barrel. The mounting hub 40 may have a second mounting structure 42 which is complementary to the first mounting structure 28 on the transition portion of the barrel to removably mount the needle on the barrel. In some embodiments, the second mounting structure 42 may utilize a friction connection and may comprise a slight taper in the width of an inner surface of the mounting hub. Optionally, the second mounting structure may comprise threads formed on the interior of the hub 40 that are complementary to threads on the transition portion.

Optionally, the mounting hub 40 may include a rotation resisting structure 44 which is configured to resist rotation of the needle device 32 with respect to, for example, a cap covering the needle. In some embodiments, the rotation resisting structure 44 may comprise at least one longitudinal rib formed on the exterior surface of the mounting hub 40, and may include a plurality of the longitudinal ribs.

The needle exchange device 50 generally provides a place to dispose of a used needle from the syringe while holding a new needle to be mounted on the syringe. The exchange device 50 may form a pair of needle sheaths 52, 54, with one of the needle sheaths functioning as a disposal sheath for receiving a needle device to be disposed of, and the other of the needle sheaths functioning as a dispensing sheath for dispensing a needle device to be used on the syringe. In general, the needle exchange device 50 has opposite first 56 and second 57 ends, and may be elongated along a longitudinal axis 58.

Each of the needle sheaths may have a sheath interior 60 with a channel 62 for receiving the needle 34 and at least a portion of the mounting hub 40 of a needle device. The channel 62 may extend along an axis substantially parallel to the longitudinal axis 58 of the device. The channel of each sheath 52, 54 may have an insertion opening 64 which may be located at an insertion end 66 of the respective sheath and positioned opposite of a blind end 68 of the sheath such that the channel extends between the insertion end 66 and the blind end 68. Each needle sheath may be formed by a perimeter wall 70 with an inner surface 72, and the inner surface may define a width across the channel 62 which may taper narrower from the insertion end 66 toward the blind end 68. An end wall 74 may close the blind end 68 of the channel with a perimeter wall 70.

One advantageous feature of the needle exchange device 50 is that the sheaths may be substantially oppositely oriented on the device 50. The respective insertion openings 64 of the needle sheaths 52, 54 may be located on longitudinally opposite points of the exchange device 50. In some embodiments, the channels 62 of the needle sheaths 52, 54 may be aligned with the same longitudinal axis and the sheaths may be positioned substantially end-to-end with respect to each other (see FIGS. 1 and 2). In other embodiments, the channels of the needle sheaths may be positioned side-by side (see FIGS. 4 and 5).

In some aspects, the needle exchange device 50 may have an unused (or initial) condition and a used (or final) condition. The unused condition of the needle exchange device 50 may be characterized by the disposal sheath 54 being substantially or completely empty and an unused needle device 32 being positioned in the dispensing sheath 52. The used condition of the exchange device 50 may be characterized by the dispensing sheath 52 being substantially or completely empty and a used needle device 32 being positioned in the disposal sheath 54.

The needle exchange device 50 may also include a finger shield 80 which is positioned on one of the needle sheath 52, 54 to protect the fingers of a user gripping the needle exchange device during use. The finger shield 80 may be positioned on the disposal sheath 54 to protect the user's fingers during insertion of a used needle device into the disposal sheath. The finger shield may be positioned adjacent to the insertion opening 64 of the disposal sheath, and may extend radially outwardly from the insertion end, and may have a substantially annular configuration.

In use, a user may grip the needle exchange device 50, and may position his or her fingers behind the finger shield 80 if the device 50 is so equipped. The user may insert the used needle of a vaccination apparatus (such as a syringe or syringe-like vaccination gun) into the insertion opening 64 on the insertion end 66 of the disposal needle sheath 54 of the device 50 so that the rotation resisting structure 44 on the hub 40 of the used needle device engages structure on the disposal needle sheath, such as on the inner surface 72 of the perimeter wall. Rotation of the needle device typically dislodges the friction connection between the second mounting structure 42 on the hub 40 and the first mounting structure 28 on the barrel so that the hub 40 of the used needle device is freed from the syringe, leaving the used needle device in the disposal needle sheath 54.

The user may then turn the exchange device 50 around with respect to the syringe so that the dispensing needle sheath 52, and the unused needle device therein, is proximate to the transition portion 22 and the first mounting structure 28 of the syringe. A portion of the barrel of the syringe may be inserted into the mounting hub 40 of the unused needle device in the dispensing needle sheath 52 so that the first mounting structure 28 on the barrel engages with the second mounting structure 42 on the hub 40 to create a secured or mounted condition therebetween. The needle device on the syringe may then be withdrawn or pulled out of the interior 60 of the dispensing sheath 52 and the syringe (or other vaccination device) is ready for use. The used needle device is nested within the disposal needle sheath 54, and may be disposed in an appropriate manner without significant danger to the user of an unintentional stick.

As illustratively shown in FIGS. 6 through 9, some implementations of the system may provide a needle exchange device 110 which has the ability to utilize a needle assembly 90 as a prepackaged unit so that the user may avoid having to remove a needle device from packaging used to supply the needle device to a user. Significantly, the configuration of the needle exchange device to some extent permits the incorporation of the needle assembly into needle exchange device so that the needle device only needs to be removed from the needle assembly at the time of actual use of the needle device, such as the time of mounting the needle device onto the syringe.

While the configurations of the needle assembly 90 may vary depending upon the source or supplier of the needle assembly, the needle assembly may typically include the needle device 32 as well as a protective sleeve 92 for removably receiving at least a portion of the needle device 32 during the period prior to use of the needle device, such as during storage prior to use of the needle device for injection. For example, the protective sleeve 92 may have a configuration that permits it to receive at least the needle 34 of the needle device 32 for protecting the physical integrity and preserving the cleanliness of the needle, while also protecting a person handling the needle device from unintentional and accidental sticks. The protective sleeve 92 may define an elongated needle chamber into which is inserted at least the needle (and optionally additional portions of the needle device). The protective sleeve 94 may be elongated and have a mouth 96 into which the portions of the needle device are inserted and from which the needle device is withdrawn just prior to use of the needle. The protective sleeve 92 may have a closed end located on the sleeve opposite of the mouth 96. The protective sleeve 92 has an exterior surface 98 which may have various features for enhancing the grippability of the sleeve such as, for example, one or more longitudinally-extending ribs 100, 102.

The needle assembly may also include a protective cap 104 for removably positioning over a portion of the protective sleeve 92, such as the portion of the protective sleeve located about the mouth 96 of the sleeve. The protective cap 104 may be positionable over any portion of the needle device 32 which protrudes from the mouth of the protective sleeve when the needle device is inserted in the sleeve. Illustratively, the protective cap 104 may have an open end 106 which is configured to receive a portion of the protective sleeve and a closed end 108 which is located opposite of the open end 106.

The needle exchange device 110 may facilitate exchange of needle devices on syringes and in particular, the removal of a needle device from a syringe and then the mounting of a distinct needle device on the syringe from needle protection elements of the needle assembly 90 such as the protective sleeve 92 and the protective cap 104. In such embodiments, the exchange device 110 may be configured to engage elements of the needle assembly 90, such as the protective sleeve 92 of the needle assembly, rather than engaging, for example, the needle device directly. Such a configuration may be advantageous in that commercially available needle assemblies 90 (including the needle device 32, the protective sleeve 92 and the protective cap 104) obtainable by the user separate of the needle exchange device 110 may be used with the exchange device, and the needle assembly may be mounted on the needle exchange device prior to executing the exchange of needles devices on a syringe without removing the needle device from the protective sleeve 92.

The needle exchange device 110 may form at least one needle sheath 112 which is utilized as a disposal sheath for receiving a needle device 32 needing to be disposed of after usage is completed. The needle sheath 112 may have characteristics similar to the needle sheath 54 described herein, including the elongated channel 62. The needle exchange device 110 may also include a finger shield 80 which extends outwardly from the insertion opening 64 of needle sheath 112 to help protect the fingers of the user gripping the perimeter wall 70 of the sheath as the used needle device is inserted into the sheath 112.

In general, the needle exchange device 110 may be elongated with opposite first 116 and second 117 ends positioned along a longitudinal axis 118 of the device 110. The axis along which the channel 62 of the sheath 112 extends may be oriented substantially parallel to the axis 118 of the device 110, and the insertion opening 64 of the of the sheath 112 may be located at the first end of the device 110.

The needle exchange device 110 may also form a needle assembly pocket 113 for removably receiving at least a portion of the needle assembly 94 incorporating the needle device to be mounted on and used on a syringe after removal of another needle device to the disposal sheath. The needle assembly pocket 113 may define an elongated dispensing cavity 114 configured to removably receive a portion of the protective sleeve 92 of the needle assembly 90. The dispensing cavity 114 may have a cavity opening 120 and a closed end 122 located opposite of the opening 120 such that the cavity extends between the opening 120 and the end 122. The length of the elongated dispensing cavity 114 may be sufficiently long to receive a suitable portion of the protective sleeve 92 of the needle assembly to permit the protective sleeve to be frictionally attached to or lodged in or otherwise engaged with the interior surfaces of the dispensing cavity 114 to hold the protective sleeve from unintentional removal of the sleeve 92 from the dispensing cavity 114, at least not without the application of a significant pulling force applied by, for example, the hand of the user. In some embodiments, the width of the dispensing cavity 114 may decrease or narrow to some degree moving from the cavity opening 120 toward the closed end 122 to facilitate lodging of the protective sleeve 92 in the cavity 114.

The axis along which the dispensing cavity 114 extends may be oriented substantially parallel to the longitudinal axis 118 of the device 110 such that the length dimension of the elongated dispensing cavity and the length dimension of the elongated channel of the needle sheath may be oriented substantially parallel to each other. Further, the needle sheath 112 may have an opposite orientation with respect to the dispensing cavity 114 of the needle assembly pocket 113 such that the cavity opening 120 of the dispensing cavity is located at the second end 117 of the device 110 opposite of the insertion opening 64 of the needle sheath 112 located at the first end 116.

It should be appreciated that in the foregoing description and appended claims, that the terms "substantially" and "approximately," when used to modify another term, mean "for the most part" or "being largely but not wholly or completely that which is specified" by the modified term.

It should also be appreciated from the foregoing description that, except when mutually exclusive, the features of the various embodiments described herein may be combined with features of other embodiments as desired while remaining within the intended scope of the disclosure.

Further, those skilled in the art will appreciate that steps set forth in the description and/or shown in the drawing figures may be altered in a variety of ways. For example, the order of the steps may be rearranged, substeps may be performed in parallel, shown steps may be omitted, or other steps may be included, etc.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated.

With respect to the above description then, it is to be realized that the optimum dimensional relationships for the parts of the disclosed embodiments and implementations, to include variations in size, materials, shape, form, function and manner of operation, assembly and use, are deemed readily apparent and obvious to one skilled in the art in light of the foregoing disclosure, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosed subject matter to the exact construction and operation shown and described, and accordingly, all suitable modifications and equivalents may be resorted to that fall within the scope of the claims.

We claim:

1. A system for facilitating exchange of needles on syringes, the system comprising:
   a needle exchange device elongated along a longitudinal axis with opposite first and second ends, the needle exchange device forming a needle receiving sheath for receiving at least a portion of a needle device mounted on a syringe to be discarded, the needle receiving sheath defining an insertion opening and an elongated channel in communication with the insertion opening to receive the at least a portion of a needle device, the needle exchange device forming a needle assembly dispensing pocket defining an elongated dispensing cavity and having a cavity opening; and
   a needle assembly at least partially received in the dispensing cavity of the needle assembly dispensing pocket of the needle exchange device, the needle assembly being removable as a unit from the needle assembly dispensing pocket, the needle assembly including:
      a needle device with a needle; and
      a protective sleeve positioned over at least the needle of the needle device;
   wherein the needle receiving sheath of the needle exchange device is empty of any needle device such that the needle receiving sheath is ready to accept a needle device from a syringe;
   wherein an axis along which the channel of the needle receiving sheath is elongated and an axis along which the cavity of the needle assembly dispensing pocket is elongated are oriented substantially parallel to the longitudinal axis of the needle exchange device;
   wherein the needle receiving sheath and the needle assembly dispensing pocket are substantially oppositely oriented on the exchange device such that the insertion opening of the needle receiving sheath is located at the first end of the needle exchange device and the cavity opening of the needle assembly dispensing pocket is located at the second end of the needle exchange device opposite of the insertion opening;
   wherein an interior of the dispensing cavity of the needle assembly dispensing pocket is differently configured from an interior of the elongated channel of the needle receiving sheath to facilitate at least partial insertion of the protective sleeve of the needle assembly and to facilitate insertion of the needle device without the protective sleeve in the elongated channel of the needle receiving sheath for disposal; and
   wherein a cross-section of an interior of the needle assembly dispensing pocket has a rectangular shape configured to engage an exterior of the protective sleeve of the protective device of the needle assembly; and
   wherein a cross-section of an interior of the needle receiving sheath has a substantially circular shape to engage an exterior of a needle device on a syringe.

2. The system of claim 1 wherein the needle receiving sheath of the needle exchange device has a transverse width and the needle assembly dispensing pocket has a transverse width and longitudinal length, the transverse width of the needle assembly dispensing pocket being greater at all points along the longitudinal length of the needle assembly dispensing pocket than the transverse width of the needle receiving sheath.

3. The system of claim 1 wherein the needle receiving sheath of the needle exchange device has an exterior surface with a substantially circular cross sectional shape; and
   wherein the needle assembly dispensing pocket of the needle exchange device has an exterior surface with a substantially rectangular cross-sectional shape.

4. The system of claim 1 wherein the elongated channel of the needle receiving sheath and the dispensing cavity of the needle assembly dispensing pocket are positioned side-by-side.

5. The system of claim 1 wherein the channel of the needle receiving sheath has a blind end located opposite of the insertion opening and the cavity of the needle assembly dispensing pocket has a closed end opposite of the cavity opening.

6. The system of claim 1 additionally comprising a syringe including a plunger and a barrel with a main portion defining a major portion of an interior of the barrel and a transition portion, the transition portion having a first mounting structure; and
   a syringe needle device removably mounted on the syringe, the syringe needle device comprising a needle and a mounting hub, the mounting hub having a second mounting structure complementary to the first mounting structure and configured to removably mount on the transition portion of the barrel, the syringe needle device being positionable in the needle receiving sheath of the needle exchange device.

7. A system for facilitating exchange of needles on syringes, the system comprising:
   a needle exchange device elongated along a longitudinal axis with opposite first and second ends, the needle exchange device forming a needle receiving sheath for receiving at least a portion of a needle device mounted on a syringe to be discarded, the needle receiving sheath defining an insertion opening and an elongated channel in communication with the insertion opening to receive the at least a portion of a needle device, the needle exchange device forming a needle assembly dispensing pocket defining an elongated dispensing cavity and having a cavity opening, the channel of the needle receiving sheath has a blind end located opposite of the insertion opening and the cavity of the needle assembly dispensing pocket has a closed end opposite of the cavity opening, a finger shield positioned at the first end of the needle exchange device and extending radially outwardly from the insertion opening of the needle receiving sheath to protect fingers of the user gripping the needle exchange device; and
   a needle assembly at least partially received in the dispensing cavity of the needle assembly dispensing pocket of the needle exchange device, the needle assembly being removable as a unit from the needle assembly dispensing pocket, the needle assembly including:
      a needle device with a needle; and
      a protective sleeve positioned over at least the needle of the needle device;
   wherein the needle receiving sheath of the needle exchange device is empty of any needle device such that the needle receiving sheath is ready to accept a needle device from a syringe;
   wherein an axis along which the channel of the needle receiving sheath is elongated and an axis along which the cavity of the needle assembly dispensing pocket is elongated are oriented substantially parallel to the longitudinal axis of the needle exchange device;

wherein the needle receiving sheath and the needle assembly dispensing pocket are substantially oppositely oriented on the exchange device such that the insertion opening of the needle receiving sheath is located at the first end of the needle exchange device and the cavity opening of the needle assembly dispensing pocket is located at the second end of the needle exchange device opposite of the insertion opening;

wherein an interior of the dispensing cavity of the needle assembly dispensing pocket is differently configured from an interior of the elongated channel of the needle receiving sheath to facilitate at least partial insertion of the protective sleeve of the needle assembly and to facilitate insertion of the needle device without the protective sleeve in the elongated channel of the needle receiving sheath for disposal; and wherein the elongated channel of the needle receiving sheath and the dispensing cavity of the needle assembly dispensing pocket are positioned side-by-side.

8. The system of claim 7 additionally comprising a finger shield positioned toward the first end of the needle exchange device about the insertion opening of the needle receiving sheath to protect fingers of the user gripping the needle exchange device.

9. The system of claim 8 wherein the finger shield is positioned on the needle receiving sheath to protect the fingers of the user during insertion of a needle device into the insertion opening of the needle receiving sheath after use of the needle device.

10. The system of claim 8 wherein the finger shield is positioned adjacent to the insertion opening of the needle receiving sheath.

11. The system of claim 8 wherein the finger shield extends radially outwardly from the insertion opening of the needle receiving sheath.

12. The system of claim 8 wherein the finger shield has an outer peripheral edge, the outer peripheral edge having a substantially annular configuration.

13. The system of claim 7 wherein the needle receiving sheath of the needle exchange device has a transverse width and the needle assembly dispensing pocket has a transverse width and longitudinal length, the transverse width of the needle assembly dispensing pocket being greater at all points along the longitudinal length of the needle assembly dispensing pocket than the transverse width of the needle receiving sheath.

14. The system of claim 13 wherein a cross-section of an interior of the needle assembly dispensing pocket has a rectangular shape configured to engage an exterior of the protective sleeve of the protective device of the needle assembly; and wherein a cross-section of an interior of the needle receiving sheath has a substantially circular shape to engage an exterior of a needle device on a syringe.

15. The system of claim 14 wherein the needle receiving sheath of the needle exchange device has an exterior surface with a substantially circular cross sectional shape; and wherein the needle assembly dispensing pocket of the needle exchange device has an exterior surface with a substantially rectangular cross-sectional shape.

16. A system for facilitating exchange of needles on syringes, the system comprising:

a needle exchange device elongated along a longitudinal axis with opposite first and second ends, the needle exchange device forming a needle receiving sheath for receiving at least a portion of a needle device mounted on a syringe to be discarded, the needle receiving sheath defining an insertion opening and an elongated channel in communication with the insertion opening to receive the at least a portion of a needle device, the needle exchange device forming a needle assembly dispensing pocket defining an elongated dispensing cavity and having a cavity opening, the channel of the needle receiving sheath has a blind end located opposite of the insertion opening and the cavity of the needle assembly dispensing pocket has a closed end opposite of the cavity opening, a finger shield positioned at the first end of the needle exchange device and extending radially outwardly from the insertion opening of the needle receiving sheath to protect fingers of the user gripping the needle exchange device; and wherein the needle receiving sheath of the needle exchange device is empty of any needle device such that the needle receiving sheath is ready to accept a needle device from a syringe;

wherein an axis along which the channel of the needle receiving sheath is elongated and an axis along which the cavity of the needle assembly dispensing pocket is elongated are oriented substantially parallel to the longitudinal axis of the needle exchange device;

wherein the needle receiving sheath and the needle assembly dispensing pocket are substantially oppositely oriented on the exchange device such that the insertion opening of the needle receiving sheath is located at the first end of the needle exchange device and the cavity opening of the needle assembly dispensing pocket is located at the second end of the needle exchange device opposite of the insertion opening;

wherein an interior of the dispensing cavity of the needle assembly dispensing pocket is differently configured from an interior of the elongated channel of the needle receiving sheath to facilitate at least partial insertion of the protective sleeve of the needle assembly and to facilitate insertion of the needle device without the protective sleeve in the elongated channel of the needle receiving sheath for disposal;

wherein the elongated channel of the needle receiving sheath and the dispensing cavity of the needle assembly dispensing pocket are positioned side-by-side; and wherein the needle receiving sheath of the needle exchange device has a transverse width and the needle assembly dispensing pocket has a transverse width and longitudinal length, the transverse width of the needle assembly dispensing pocket being greater at all points along the longitudinal length of the needle assembly dispensing pocket than the transverse width of the needle receiving sheath.

17. The system of claim 16 wherein a cross-section of an interior of the needle assembly dispensing pocket has a rectangular shape configured to engage an exterior of the protective sleeve of the protective device of the needle assembly; and wherein a cross-section of an interior of the needle receiving sheath has a substantially circular shape to engage an exterior of a needle device on a syringe.

18. The system of claim 17 wherein the needle receiving sheath of the needle exchange device has an exterior surface with a substantially circular cross sectional shape; and wherein the needle assembly dispensing pocket of the needle exchange device has an exterior surface with a substantially rectangular cross-sectional shape.

\* \* \* \* \*